(12) United States Patent
Turner

(10) Patent No.: US 12,265,448 B2
(45) Date of Patent: Apr. 1, 2025

(54) APPARATUS AND METHOD FOR DATA FAULT DETECTION AND REPAIR

(71) Applicant: EmergIP, LLC, Dover, DE (US)

(72) Inventor: Christopher Turner, Dover, DE (US)

(73) Assignee: EmergIP, LLC, Dover, DE (US)

( * ) Notice: Subject to any disclaimer, the term of this patent is extended or adjusted under 35 U.S.C. 154(b) by 0 days.

(21) Appl. No.: 18/137,682

(22) Filed: Apr. 21, 2023

(65) Prior Publication Data

US 2024/0354185 A1 Oct. 24, 2024

(51) Int. Cl.
*G06F 11/07* (2006.01)
*G06F 16/23* (2019.01)
*G16H 10/60* (2018.01)

(52) U.S. Cl.
CPC ...... *G06F 11/0793* (2013.01); *G06F 11/0721* (2013.01); *G06F 11/0775* (2013.01); *G06F 16/2365* (2019.01); *G16H 10/60* (2018.01)

(58) Field of Classification Search
CPC . G16H 10/60; G06F 11/0793; G06F 16/2365; G06F 11/0721; G06F 11/0775
See application file for complete search history.

(56) References Cited

U.S. PATENT DOCUMENTS

| | | | |
|---|---|---|---|
| 10,347,369 B1* | 7/2019 | Dudzinski | G06Q 50/22 |
| 11,315,196 B1* | 4/2022 | Narayan | G06F 18/285 |
| 2003/0083903 A1* | 5/2003 | Myers | G16H 15/00 705/2 |
| 2018/0330058 A1* | 11/2018 | Bates | G16H 50/20 |
| 2020/0019946 A1* | 1/2020 | Walker | G06Q 20/14 |
| 2020/0251198 A1* | 8/2020 | Lavender | G06N 5/01 |
| 2022/0084664 A1* | 3/2022 | Ginsburg | G16H 15/00 |
| 2022/0309592 A1* | 9/2022 | Zahora | G06Q 10/10 |
| 2022/0359067 A1* | 11/2022 | McCallum | G06Q 30/0206 |
| 2023/0317260 A1* | 10/2023 | Zahora | G16H 50/70 705/3 |

* cited by examiner

*Primary Examiner* — Courtney Harmon
(74) *Attorney, Agent, or Firm* — Caldwell Intellectual Property Law

(57) ABSTRACT

An apparatus for data fault detection and repair is disclosed. The apparatus comprises at least a processor and a memory communicatively connected to the at least a processor. The memory instructs the processor to receive a user profile relating to a user, wherein the user profile comprises at least provider data of a user. The memory instructs the processor to generate practitioner data as a function of the user profile. The memory additionally instructs the processor to retrieve remittance data as a function of the practitioner data. The memory then instructs the processor to identify a data fault in at least one of the practitioner data and the remittance data. The memory instructs the processor to initiate a data correction action based on the identified data fault.

18 Claims, 9 Drawing Sheets

APPARATUS AND METHOD FOR DATA FAULT DETECTION AND REPAIR

FIELD OF THE INVENTION

The present invention generally relates to the field of medical facility management. In particular, the present invention is directed to an apparatus and method for data fault detection and repair.

BACKGROUND

Medical providers frequently miss information regarding patients they treat given the fast pace and critical timing required when providing emergency treatment and transport. This can lead to inefficiencies, gaps, or mistakes in billing.

SUMMARY OF THE DISCLOSURE

In an aspect, an apparatus for data fault detection and repair is disclosed. The apparatus comprises at least a processor and a memory communicatively connected to the at least a processor. The memory instructs the processor to receive a user profile relating to a user, wherein the user profile comprises at least provider data of a user. The memory instructs the processor to generate practitioner data as a function of the user profile. The memory additionally instructs the processor to retrieve remittance data as a function of the practitioner data. The memory then instructs the processor to identify a data fault in at least one of the practitioner data and the remittance data. The memory instructs the processor to initiate a data correction action based on the identified data fault.

In another aspect, a method for data fault detection and repair is disclosed. The method includes receiving, using at least a processor, a user profile relating to a user, wherein the user profile comprises at least provider data of a user. The method includes generating, using the at least a processor, practitioner data as a function of the user profile. The method additionally retrieves, by the at least a processor, remittance data as a function of the practitioner data. The method additionally includes identifying, by the at least a processor, a data fault in at least one of the practitioner data and the remittance data. The method includes initiating, by the at least a processor, a data correction action based on the identified data fault.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and methods for an apparatus for data fault detection and repair. The apparatus comprises at least a processor and a memory communicatively connected to the at least a processor. The memory instructs the processor to receive a user profile relating to a user, wherein the user profile comprises at least a provider data of a user. The memory instructs the processor to generate practitioner data as a function of the user profile. The memory additionally instructs the processor to retrieve remittance data as a function of the practitioner data. The memory then instructs the processor to identify a data fault in at least one of the practitioner data and the remittance data. The memory instructs the processor to initiate a data correction action based on the identified data fault.

Figure 1:
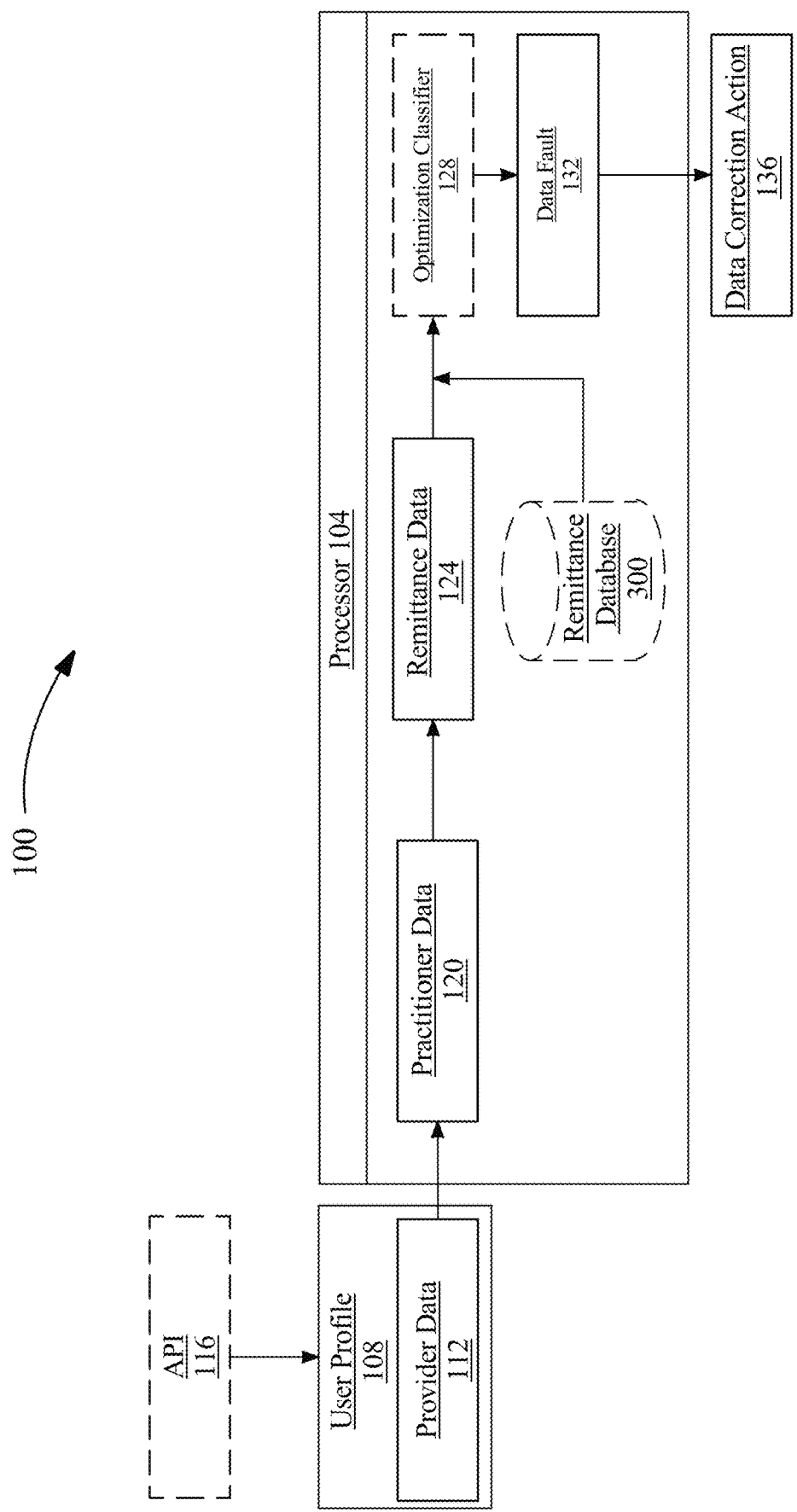
FIG. 1 is a block diagram of an exemplary embodiment of an apparatus for data fault detection and repair.

Referring now to FIG. 1, an exemplary embodiment of apparatus 100 for data fault detection and repair is illustrated. The apparatus includes a processor 104. Processor 104 may include any computing device as described in this disclosure, including without limitation a microcontroller, microprocessor, digital signal processor (DSP), and/or system on a chip (SoC) as described in this disclosure. The computing device may include, be included in, and/or communicate with a mobile device such as a mobile telephone or smartphone. Processor 104 may include a single computing device operating independently, or may include two or more computing device operating in concert, in parallel, sequentially, or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software, etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable the scalability of apparatus 100 and/or the computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, processor 104 is configured to receive a user profile 108. For the purposes of this disclosure, a "user profile" is a representation of information and/or data describing biological and/or health-related information associated with a user. The user profile may be associated with an individual or may be created by a processor 104, a user, or a third party. User profile 108 may include at least any of the following personal information: age, height, weight, heart rate, current diagnosis, medical history, allergies, current condition, current symptoms, known disorders, test results (e.g., basic metabolic panel, blood test, other physiological data, and the like), medications, growth chart, family history, and the like. For example, and without limitation, a user profile may include information about a current condition such as a reported stomach pain of a user. The user profile 108 may comprise user data. As used in the current disclosure, "user data" is data relating to the user's medical care. Medical care may be the act/attempt to improve of the user's health. User data may include provider data 112, medical history, personal information, pre-existing conditions, the physical condition of the user, biometrics of the user, the physical appearance of the user, geographic location of the user, medical transport, distance from, accident history, and the like. User data may include past/preset injuries and/or ailments that are suffered by the user. A user profile may be received by process 104 via a user input. For example, and without limitation, the user or a third party may manually input user profile 108 using a graphical user interface of processor 104 or a remote device, such as, for example, a smartphone or laptop. User profile 108 may additionally be generated via the answer to a series of questions. The series of questions may be implemented using a chatbot, as described herein below. A chatbot may be configured to generate questions regarding the user's current ailments, past ailments, medical history, family medical history, and the like. In a non-limiting embodiment, a user may be prompted to input specific information or may fill out a questionnaire. In an embodiment, a graphical user interface may display a series of questions to prompt a user for information pertaining to the user profile 108. As a further example, a chatbot may display a list of possible conditions to user, from which user may select each applicable condition the user currently suffers from. Processor 104 may receive user selection of a user autoimmune disorders and select additional autoimmune disorders as a function of the user selection. In another example, and without limitation, a medical professional or personnel may input the user profile 108 using a graphic user interface of processor 104 or a remote device. In another example, and without limitation, a third party, such as a different medical entity or healthcare provider, may transmit information of user profile 108 to processor 104. User profile 108 may be directly inputted into processor 104. User profile 108 may be transmitted to processor 104, such as via a wired or wireless communication, as previously discussed in this disclosure. User profile 108 can be retrieved from multiple sources including clinical reports, available medical facility records, insurance databases, driver's license databases, news articles, social media profiles and/or posts, etc. to determine if a user is liable for or exempt from charges, subject to reimbursement for services provided, eligible for additional coverage, and the like. A user profile may be placed through an encryption process for security purposes. This may additionally include storing a user profile 108 on an immutable sequential listing as described herein below.

With continued reference to FIG. 1, user profile 108 includes provider data 112. As used in the current disclosure, "provider data" is any element of data related to the health insurance of the user. Health insurance or medical insurance is a type of insurance that covers the whole or a part of the risk of a person incurring medical expenses. Health insurance may include Medicare and Medicaid. Provider data 112 may include the health insurance provider, policy number, deductible information, premium, co-payments, coinsurance, exclusions, coverage limits, out-of-pocket maximum, formulary, a list of prior authorizations, vision insurance, dental insurance, and the like. Provider data 112 may include the identification of a primary insurance provider and a secondary insurance provider. Provider data 112 may include a list of medical facilities that are in-network. In a non-limiting example, provider data 112 may provide an indication of if a procedure is covered by the health insurance of the user. Provider data 112 may include an indication of the type of health insurance a user has. Types of health insurance may include Health maintenance organizations (HMOs), Preferred provider organizations (PPOs), Exclusive provider organizations (EPOs), Point-of-service (POS) plans, High-deductible health plans (HDHPs), health savings accounts (HSAs), Indemnity plans, Children's Health Insurance Program (CHIP), the absence of health insurance, and coverage details regarding each. Provider data 112 may additionally comprise a listing of a payer code, wherein a payer code is an alphanumeric code that represents the identity of the health insurer. Provider data 112 may include payer rules and policies associated with the health insurer. Payer policies may be used to support coverage decisions and explain reimbursement for health care services to patients who are covered by provider data 112. These policies outline whether a medical facility or a medical provider is in-network versus out-of-network as well as how much is covered by insurance for things like office visits, surgical procedures, prescriptions, etc.

With continued reference to FIG. 1, user profile 108 may include the medical history of the user. As used in the current disclosure, "medical history" is the history of medical treatment that has been received by the user. Medical treatment may be any treatment provided by a medical facility with the goal of improving the user's health. Medical treatment may include medical evaluation, medical diagnosis, prescribing medicines/treatments, providing treatments, therapy, occupational therapy, physical therapy, care given during a hospital stay, surgery, treatment provided by a medical practitioner, and the like.

With continued reference to FIG. 1, user profile 108 may be generated using a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, processor 104 may generate a web crawler to compile the user profile 108 and user data. The web crawler may be seeded and/or trained with a reputable website, such as a medical facilities website, to begin the search. A web crawler may be generated by a processor 104. In some embodiments, the web crawler may be trained with information received from a user through a user interface. In some embodiments, the web crawler may be configured to generate a web query. A web query may include search criteria received from a user. For example, a user may submit a plurality of websites for the web crawler to search to extract medical history, user data, and past medical bills, based on criteria such as a time period, medical facility type, medical facility location, procedure type, and the like.

With continued reference to FIG. 1, processor 104 may be configured to extract user data from at least at least a medical record. As used in the current disclosure, a "medical record" is a document that contains information regarding medical treatment that has been administered to the user. Medical records may include user credentials, reports, hospital records, clinical reports, available medical facility records, insurance databases, driver's license databases, news articles, social media profiles and/or posts, and the like. Medical records may be identified using a web crawler. Medical records may include a variety of types of "notes" entered over time by healthcare professionals, recording observations and administration of drugs and therapies, orders for the administration of drugs and therapies, test results, x-rays, reports, and the like. Medical records have traditionally been compiled and maintained by healthcare providers, but advances in online data storage have led to the development of personal health records (PHR) that are maintained by patients themselves, often on third-party websites. A medical record may identify the patient and contains information regarding the patient's case history at a healthcare provider. Medical records may be converted into machine-encoded text using an optical character reader (OCR).

Still referring to FIG. 1, in some embodiments, optical character recognition or optical character reader (OCR) includes automatic conversion of images of written (e.g., typed, handwritten, or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to the image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include the removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify a script allowing an appropriate OCR algorithm to be selected. In some cases, a character isolation or "segmentation" process may separate signal characters, for example character-based OCR algorithms. In some cases, a normalization process may normalize the aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 5-7. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. The second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 5-7.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, processor 104 may receive a user profile from a third-party source using an application programming interface 116 (API). As used in the current disclosure, an "application programming interface" is a way for two or more computer programs to communicate with each other. An application programming interface 116 may be a type of software interface, offering a service to other pieces of software. In contrast to a user interface, which connects a computer to a person, an application programming interface 116 may connect computers or pieces of software to each other. An API 116 may not be intended to be used directly by a person (the end user) other than a computer programmer who is incorporating it into the software. An API 116 may be made up of different parts which act as tools or services that are available to the programmer. A program or a programmer that uses one of these parts is said to call that portion of the API 116. The calls that make up the API 116 are also known as subroutines, methods, requests, or endpoints. An API 116 specification may define these calls, meaning that it explains how to use or implement them. One purpose of API 116 may be to hide the internal details of how a system works, exposing only those parts a programmer will find useful and keeping them consistent even if the internal details later change. An API 116 may be custom-built for a particular pair of systems, or it may be a shared standard allowing interoperability among many systems. The term API 116 may be often used to refer to web APIs 116, which allow communication between computers that are joined by the internet. API 116 may be configured to query for web applications in order to retrieve user profiles 108 to another web application, data database, insurance provider database, creditor database, medical center patient portal, and the like. An API 116 may be further configured to filter through web applications according to a filter criterion. In this disclosure, "filter criteria" are conditions the web applications must fulfill in order to qualify for API 116. Web applications may be filtered based on these filter criteria. Filter criteria may include, without limitation, types of medical facilities, location of the medical facility, user attendance at the medical facility, user attendance dates at the medical facility, and the like.

With continued reference to FIG. 1, processor 104 generates practitioner data 120 as a function of the user profile 108. As used in the current disclosure, "practitioner data" is an element of data regarding the medical facility that is associated with the user. A user may be associated with a medical facility by making that facility his/her preferred facility, previous attendance or treatment at that facility, the facility being in-network for the consumer, and the like. Practitioner data 120 may include the name, location, and type of the medical facility, A medical facility may be any facility that offers health-improving services. Examples of medical facilities include, but are not limited to, hospitals, clinics, dentists offices, orthodontist offices, gynecologist offices, doctor's offices, chiropractor's offices, pediatrician's offices, surgery centers, health care centers, medical nursing homes, pharmacies, medical laboratories, medical research centers, ambulance provider, emergency medical services (EMS) providers, emergency medical services (EMS) agencies, medical transport, and the like. A medical facility may include a person, such as a physician, an organization, a hospital, an office, an ambulance, and the like. For example, and without limitation, a medical facility may refer to a physical location such as a medical building or room, or may include an organization, such as a managed care consortium and/or organization. For example, and without limitation, a medical facility may include an emergency room or department of a medical institution. In another example, and without limitation, a medical facility may include a person, such as a dentist, nurse, physician, physical therapist, surgeon, and the like. Practitioner data 120 may additionally include the types of treatment offered at the facility. In an embodiment, practitioner data 120 may be received via user input. Practitioner data 120 may be received from a user or third-party, such as a medical provider, a relative, or associate of the user. Practitioner data 120 may additionally be received by querying a database, such as database 300. Information regarding the medical facility, medical practitioners, or medical treatment that are associated with the user may be a part of the user profile 108. Processor 104 may be configured to identify and extract the practitioner data 120 from a user profile 108.

With continued reference to FIG. 1, practitioner data 120 may comprise procedure data. As used in the current disclosure, "procedure data" is any information regarding the treatment the user receives while at the facility. In an embodiment, procedure data may include the cost of the procedure incurred by the user or by the insurance provider. Procedure data may include the type of treatment, length of stay in the medical facility, cost of the procedure, cost of equipment used, and the like. Procedure data may be given in the form of an itemized medical bill. An itemized medical bill may compile each charge incurred by the user during their time at the medical facility. Procedure data may additionally include the cost of medical transportation such as non-emergency transportation and emergency transportation. Medical transportation may include Ambulatory Services, wheelchair services, stretcher flight services, medical couriers, basic life support transportation, advanced life support transportation, critical care transport, and neonatal intensive care transport.

With continued reference to FIG. 1, processor 104 may identify remittance data 124 as a function of practitioner data 120. As used in the current disclosure, "remittance data" is data regarding the billing processes and procedures of the medical facility. Remittance data 124 may include a medical bill, cost of treatment, cost of pharmaceuticals, cost of supplies, and the like. Remittance data 124 may include any past or present bill incurred by the user while visiting the medical facility. Remittance data 124 may include aggregating the medical bills. The remittance data 124 may additionally sort the medical bill according to charges. Remittance data may include any past due medical bills or any medical bills that have been sent to collections. Remittance data may be filtered according to a time frame, medical facility, types of treatment, and the like. Remittance data may additionally include a record of all medical bills that have been by an insurer or a user.

With continued reference to FIG. 1, remittance data 124 may include a remittance process. As used in the current disclosure, a "remittance process" is the medical facility's specific medical billing workflow. A medical billing workflow may have a plurality of steps including patient registration, financial responsibility identification, superbill creation, claims process, and patient statement preparation. As used in the current disclosure, "financial responsibility identification" is the process of determining which user or entity is financially responsibility for the visit. During financial responsibility identification process provider data may be evaluated along with procedure data. In a non-limiting example, generating a financial responsibility identification may include comparing provider data which indicates a coverage amount along with the covered treatments to procedure data which indicates which procedures that have been performed on a user along with the cost associated with those procedures. This process may be repeated several times if the user has multiple health insurance plans. In some embodiments, this identification may be done prior to any treatment being provided to the user. This may allow the user to compare costs between medical facilities. As used in the current disclosure, a "claims process" is the process by which claims a generated. This may include the creation of a superbill using data from a user profile 108. A super bill may include provider and clinician information, the patient's demographic information and medical history, information on the procedures and services performed, and the applicable diagnosis and procedure codes. A claims process may also include the use of a superbill to prepare a medical claim to be submitted to the patient's insurance company. Once the claim is created, the biller must go over it carefully to confirm that it meets payer and HIPPA compliance standards, including standards for medical coding and format. A claims process then may include submitting the claims to the insurance provider and the user.

With continued reference to FIG. 1, remittance data 124 may include an identification of the data category codes that were assigned to a user. As used in the current disclosure, a "data category code" is a standard code used to represent the treatment a patient received. Data category coding may also include the transformation of a healthcare diagnosis, procedures, medical services, and equipment into universal medical alphanumeric codes. The diagnoses and procedure codes may be taken from medical record documentation, such as transcription of physician's notes, laboratory, and radiologic results, etc. One or more data category codes may be generated after each encounter a user has with a medical provider. The medical providers may review the users complaint and medical history, makes an expert assessment of what is wrong and how to treat the user, and documents the entire visit. That documentation may be transformed into data category codes. In other embodiments, data category codes may be used to identify what services a medical provider provided to a user. Examples of data category coding systems may include International Classification of Diseases (ICD), Healthcare Common procedural Coding System (HCPCS), Current Procedural Terminology (CPT), International Classification of Diseases for Oncology, code on dental procedures and nomenclature, healthcare procedural coding system, modifiers, national drug codes, MS-DRG, Medical Severity Diagnosis Related Groups, Ambulatory Payment Categories. The use of data category codes may allow insurance providers and other billing agencies to map equivalencies across different service providers who may use different terminologies or abbreviations in their written claims forms, and be used to justify reimbursement of fees and expenses. Data category codes may cover topics related to diagnoses, procedures, pharmaceuticals, therapy, or medical imaging. The data category codes may also be divided into specialties in a non-limiting example cardiology, gastroenterology, nephrology, neurology, pulmonology, or orthopedic care.

With continued reference to FIG. 1, processor 104 may be configured to identify a data fault 132 within the remittance data 124 or the practitioner data 120. As used in the current disclosure, a "data fault" is an error or discrepancy within data. A data fault may include, without limitation, an error within the remittance data 124 or the practitioner data 120. This discrepancy may be described as a function of data category codes, provider data 112, medical billing, and the like. A data fault 132 may additionally include the billing procedures as applied to the user. In some embodiments, a data fault 132 may include the identification of missing or incorrect data within the user profile 108 or practitioner data 120. A data fault 132 may include an omission of the name of the medical provider, including the name of the medical facility or the name of the medical practitioner that assisted the patient. A data fault 132 also may include missing information associated with the medical practitioner including title, qualifications, notes regarding patient treatment, treatment performed, and the like. In a non-limiting example, practitioner data 120 may indicate that the medical practitioner is an EMS provider. A data fault 132 may include an omission of documentation from a EMS provider, including a missing name or job title of the EMS provider. In another non-limiting example, a data fault 132 may include an omission of information associated with the user profile 108. This may include information regarding the patient's name, address, age, sex, height, weight, physical appearance, physical condition, and the like. A data fault 132 may additionally identify that a user overbilled for a given procedure or that the chargers on the user's bill was unjustified. A data fault 132 may identify/verify what a medical insurer should pay towards the medical bills according to the provider data 112. A data fault 132 may comprise a search for a remittitur of the remittance data 124. In a non-limiting example, a data fault 132 may be identified by comparing, using processor 104 or a machine learning model, remittance data 124 comprised of data category codes to a provider data 112. The comparison may indicate what portion of the medical bill was covered under provider data 112 and any errors in payment. In an embodiment, this may include a comparison of the data category codes against a list of covered data category codes within provider data 112. In another embodiment, this may include searching through the data category codes for duplicate or inaccurate codes. Processor 104 may compare an itemized bill to a data category code associated with each treatment, with the goal of identifying a data fault 132 in the assignment of the data category code. Processor 104 may additionally be configured to compare the itemized bill to the user profile 108 and procedure data, with the goal of identifying any additional data faults 132. Processor 104 may additionally be configured to compare the data category codes to the medical provider's notes as represented in procedure data. In a non-limiting example, if the procedure data indicates that a user received emergency medical transport from their home to a medical facility, wherein the emergency medical transport charges patients by the mile for travel. User profile 108 may note that the user's home is 4 miles from the medical facility, whereas the user was charged for a trip of 7 miles. The data fault 132 may include the discrepancy in the charges by the medical provider. A data correction action 136 may be configured to generate an automatic dispute the charges by the medical provider. In another non-limiting example, remittance data 124 may indicate that data category codes relating to a kidney transplant was assigned to the user. However, through the user profile 108 and a comparison to the procedure data it is discovered that the user never received a donor's kidney. An identified data fault 132 may highlight this discrepancy. In a third non-limiting example, a provider data 112 may indicate that a given set of data category codes are covered by the user's medical insurer. The remittance data 124 may additionally indicate that the user must pay out of pocket for these charges. An identified data fault 132 may indicate that the user is not obligated to pay the additional charges.

With continued reference to FIG. 1, a processor 104 may identify a data fault 132 using a lookup table. A "lookup table," for the purposes of this disclosure, is a data structure, such as without limitation an array of data, that maps input values to output values. A lookup table may be used to replace a runtime computation with an indexing operation or the like, such as an array indexing operation. A look up table may be configured to pre-calculate and store data in a static program storage, calculated as part of a program's initialization phase, or even stored in hardware in application-specific platforms. Data within the lookup table may include previous examples of remittance data 124 compared to plan data 112 that have found data faults 132. Data within the lookup table may be received from database 300. Lookup tables may also be used to identify a data fault 132 by matching an input value to an output value by matching the input against a list of valid (or invalid) items in an array. In a non-limiting example, plan data 112 may provide that insurer must pay for procedures linked to data category codes ABC123 and ABC321 under the user's current health insurance plan. Remittance data 124 may show that data category code ABC123 was attributed to the treatment that was received by the user. However, the insurer is refusing to pay for the user's procedure. A lookup table may lookup the user's plan data 112 and remittance data 124 as inputs and output a data fault 132 indicating that the insurer must pay for the user's procedure. In another non-limiting example, a remittance data look up table may be able to associate data category codes relating to the user profile 108 to procedure data to identify a data fault. Processor 104 may be configured to "lookup" or input one or more user profile 108, provider data 112, practitioner data 120, remittance data 124, data fault 132, data category codes, procedure data, and the like. Whereas the output of the lookup table may comprise a data fault 132. Data from the lookup table may be compared to remittance data, for instance and without limitation using string comparisons, numerical comparisons such as subtraction operations, or the like; discrepancies may indicate data faults. Alternatively or additionally, a query representing elements of remittance data may be submitted to the lookup table and/or a database, and an associated data fault identifier stored in a data record within the lookup table and/or database may be retrieved using the query.

With continued reference to FIG. 1, processor 104 may identify a data fault 132 using a fault classifier 128. Fault classifier 128 may be consistent with the classifier described below in FIG. 2. Inputs to the fault classifier 128 may include user profile 108, provider data 112, practitioner data 120, remittance data 124, examples of data faults 132, data category codes, procedure data, examples of data correction actions 136, and the like. Outputs to the fault classifier 128 may include data faults 132, data fault rank, and data correction actions 136. Fault training data is a plurality of data entries containing a plurality of inputs that are correlated to a plurality of outputs for training a processor by a machine-learning process to classify remittance data 124 to practitioner data 120 or classify provider data 112 to a data category code. Fault training data may comprise data entries correlating remittance data 124 to practitioner data 120. Fault training data may be received from database 300. Fault training data may contain information about user profile 108, provider data 112, practitioner data 120, remittance data 124, examples of data faults 132, data category codes, procedure data, examples of data correction actions 136, and the like. Fault training data may be generated from any historical versions of data described herein. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, processor 104 may be configured to generate a data fault rank. As used in the current disclosure, a "data fault rank" is a scoring of the significance of the data fault 124. The significance of the data fault 124 may be related to the magnitude of the potential monetary reduction to the user's out-of-pocket costs or medical bills. The significance of the data fault 124 may additionally be related to the likelihood that a user will receive a reduction in his/her medical expenses. In a non-limiting example, a data fault rank may denote the degree of likelihood a reduction of a user's out of pocket expenses will occur as a function of data fault 124. A data fault rank may be calculated using a numerical scale. A non-limiting example, of a numerical scale, may include a scale from 1-10, 1-100, 1-1000, and the like, wherein a rating of 1 may represent a less favorable chance at a medical bill reduction, whereas a rating of 10 may represent a highly favorable chance at a medical bill reduction. A data fault rank may be generated from data fault 132, remittance data 124, and practitioner data 120, provider data 112, and the like. In a non-limiting example, a data fault rank may reflect the amount of the reduction compared to the degree of likelihood of a reduction of a medical bill. A data fault rank may be generated using a machine learning model. The machine learning model may be trained using rank training data. Rank training data may include a plurality of data entries containing a plurality of inputs that are correlated to a plurality of outputs for training a processor by a machine-learning process to classify remittance data 124 to practitioner data 120. Rank training data may comprise data entries correlating remittance data 124 to practitioner data 120. Rank training data may be received from database 300. Rank training data may contain information about user profile 108, provider data 112, practitioner data 120, remittance data 124, data faults 132, data category codes, procedure data, examples of data fault rankings, and the like. Rank training data may additionally be generated from any historical versions of any data described herein.

Still referring to FIG. 1, processor may be configured to generate a machine learning model, such as fault classifier 128, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. processor 104 may then calculate a likelihood table by calculating probabilities of different data entries and classification labels. processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a machine learning model, such as fault classifier 128, using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number experience of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, processor 104 is configured to initiate a data correction action 136 as a function of the data fault 132. As used in the current disclosure, a "data correction action" is an element of data describing an action to address the data fault 132. A data correction action 136 may include instructions to display a data fault on a display device. A data correction action 136 may include instructions to notify the user, medical provider, insurer, or the state insurance commissioner of the data fault 132. A data correction action 136 may include automatically disputing wrongful charges to a user; this may include a request for a reduction of the total for the medical bill or filling out a dispute form for medical bills with a medical provider or a collections agency. Notifying an insurer or a medical provider may include providing them with remittance data 132, plan data 112, and/or associated data fault 132. A data correction action 136 may additionally include requesting an itemized bill from a medical provider and instructing the user to carefully review the bill. A data correction action 136 may additionally include transmitting a message to a medical provider or a billing company associated with the medical provider to seek a remitter of charges as a function of a data fault 132. This may include sending a notification such as a letter, email, message, and the like, to inform a medical provider of a discrepancy. A data correction action 136 may additionally comprise notifying a medical provider and/or medical insurer of details surrounding provider data 116. In a non-limiting example, a data fault 132 may indicate that a user was overcharged for medical treatment. Data fault 132 additionally may indicate that a user's medical insurance was supposed to cover the expenses as described in provider data 112 associated with the user. A data correction data 136 may notify both the medical insurer and the medical provider that the user is not responsible for the additional charges.

Still referring to FIG. 1, processor 104 may be configured to display the data fault 132 or a data correction action 136 using a display device. As used in the current disclosure, a "display device" is a device that is used to display a content processor 104. A display device may include a user interface. A "user interface," as used herein, is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof and the like. A user interface may include a smartphone, smart tablet, desktop, or laptop operated by the user. In an embodiment, user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull down menu. When any option is clicked in this menu, then the pull down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

Figure 2:
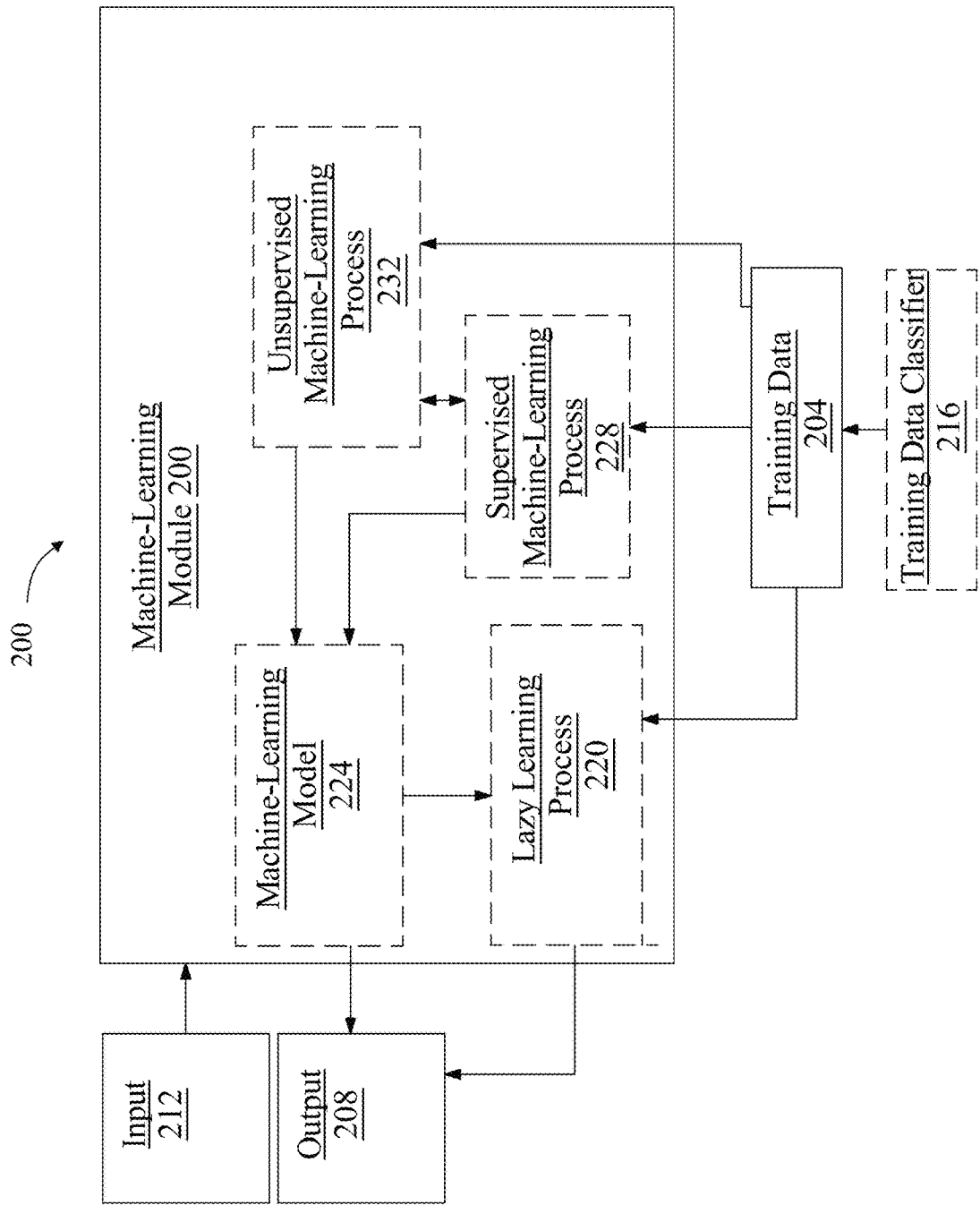
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 3:
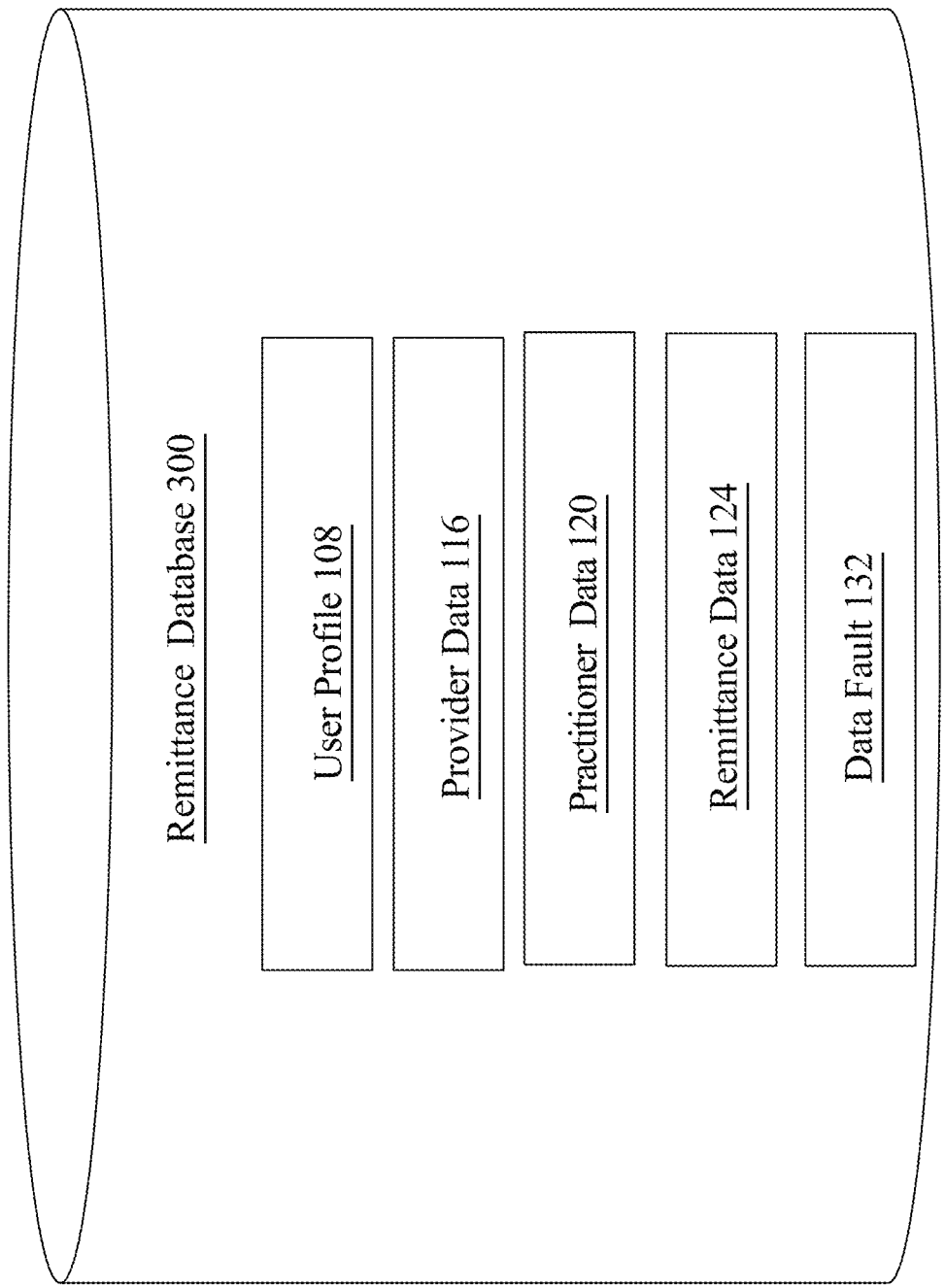
FIG. 3 is a block diagram of an exemplary embodiment of a remittance database.

Now referring to FIG. 3, an exemplary remittance database 300 is illustrated by way of block diagram. In an embodiment, any past or present versions of data disclosed herein may be stored within remittance database 300, include user profile 108, provider data 112, practitioner data 120, remittance data 124, data fault 132, data correction action 136, data category codes, procedure data, and the like. Processor 104 may be communicatively connected with remittance database 300. For example, in some cases, database 300 may be local to processor 104. Alternatively or additionally, in some cases, database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. Remittance database 300 may be implemented, without limitation, as a relational database, a key-value retrieval database such as a NOSQL database, or any other format or structure for use as a database that a person skilled in the art would recognize as suitable upon review of the entirety of this disclosure. Remittance database 300 may alternatively or additionally be implemented using a distributed data storage protocol and/or data structure, such as a distributed hash table or the like. Remittance database 300 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 4:
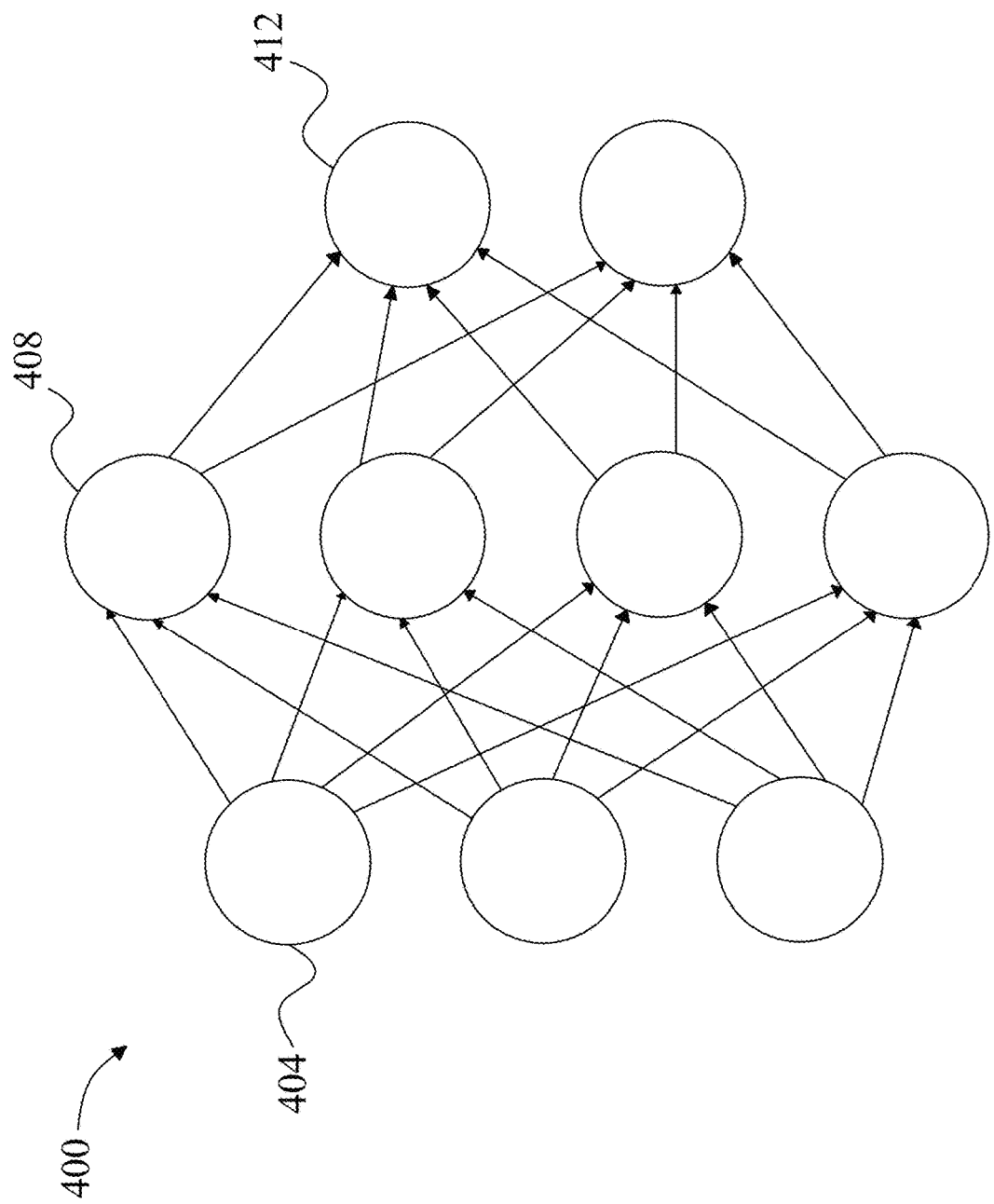
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
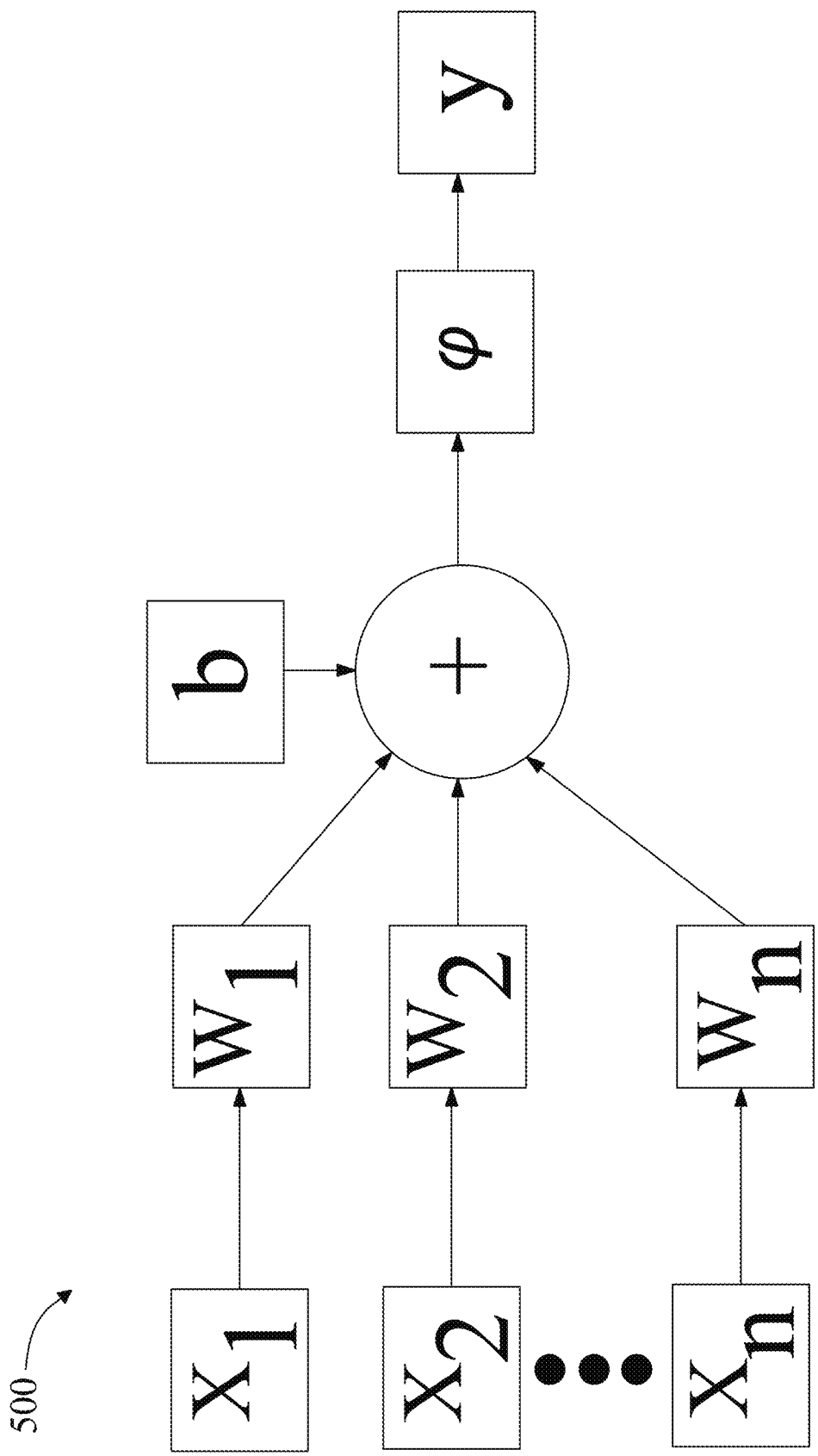
FIG. 5 is a diagram of an exemplary embodiment of a node of a neural network.

Referring now to FIG. 5, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
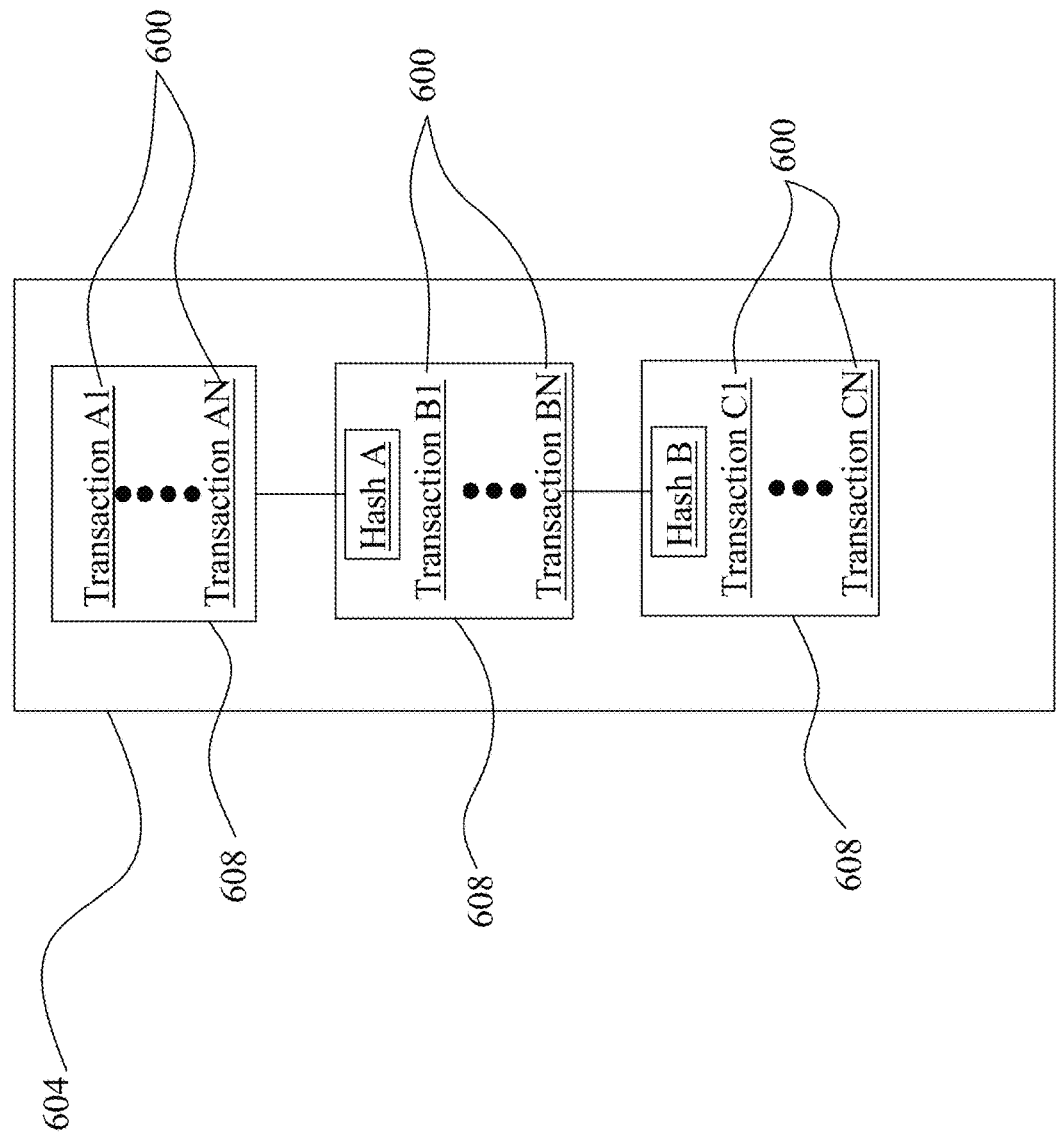
FIG. 6 is an illustration of an exemplary embodiment of an immutable sequential listing.

Referring now to FIG. 6, an exemplary embodiment of an immutable sequential listing is illustrated. An "immutable sequential listing," as used in this disclosure, is a data structure that places data entries in a fixed sequential arrangement, such as a temporal sequence of entries and/or blocks thereof, where the sequential arrangement, once established, cannot be altered, or reordered. An immutable sequential listing may be, include and/or implement an immutable ledger, where data entries that have been posted to the immutable sequential listing cannot be altered. Data elements are listing in immutable sequential listing; data elements may include any form of data, including textual data, image data, encrypted data, cryptographically hashed data, and the like. Data elements may include, without limitation, one or more at least a digitally signed assertions. In one embodiment, a digitally signed assertion 604 is a collection of textual data signed using a secure proof as described in further detail below; secure proof may include, without limitation, a digital signature as described above. Collection of textual data may contain any textual data, including without limitation American Standard Code for Information Interchange (ASCII), Unicode, or similar computer-encoded textual data, any alphanumeric data, punctuation, diacritical mark, or any character or other marking used in any writing system to convey information, in any form, including any plaintext or cyphertext data; in an embodiment, collection of textual data may be encrypted, or may be a hash of other data, such as a root or node of a Merkle tree or hash tree, or a hash of any other information desired to be recorded in some fashion using a digitally signed assertion 604. In an embodiment, collection of textual data states that the owner of a certain transferable item represented in a digitally signed assertion 604 register is transferring that item to the owner of an address. A digitally signed assertion 604 may be signed by a digital signature created using the private key associated with the owner's public key, as described above.

Still referring to FIG. 6, a digitally signed assertion 604 may describe a transfer of virtual currency, such as cryptocurrency as described below. The virtual currency may be a digital currency. Item of value may be a transfer of trust, for instance represented by a statement vouching for the identity or trustworthiness of the first entity. Item of value may be an interest in a fungible negotiable financial instrument representing ownership in a public or private corporation, a creditor relationship with a governmental body or a corporation, rights to ownership represented by an option, derivative financial instrument, commodity, debt-backed security such as a bond or debenture or other security as described in further detail below. A resource may be a physical machine e.g. a ride share vehicle or any other asset. A digitally signed assertion 604 may describe the transfer of a physical good; for instance, a digitally signed assertion 604 may describe the sale of a product. In some embodiments, a transfer nominally of one item may be used to represent a transfer of another item; for instance, a transfer of virtual currency may be interpreted as representing a transfer of an access right; conversely, where the item nominally transferred is something other than virtual currency, the transfer itself may still be treated as a transfer of virtual currency, having value that depends on many potential factors including the value of the item nominally transferred and the monetary value attendant to having the output of the transfer moved into a particular user's control. The item of value may be associated with a digitally signed assertion 604 by means of an exterior protocol, such as the COLORED COINS created according to protocols developed by The Colored Coins Foundation, the MASTERCOIN protocol developed by the Mastercoin Foundation, or the ETHEREUM platform offered by the Stiftung Ethereum Foundation of Baar, Switzerland, the Thunder protocol developed by Thunder Consensus, or any other protocol.

Still referring to FIG. 6, in one embodiment, an address is a textual datum identifying the recipient of virtual currency or another item of value in a digitally signed assertion 604. In some embodiments, address is linked to a public key, the corresponding private key of which is owned by the recipient of a digitally signed assertion 604. For instance, address may be the public key. Address may be a representation, such as a hash, of the public key. Address may be linked to the public key in memory of a computing device, for instance via a "wallet shortener" protocol. Where address is linked to a public key, a transferee in a digitally signed assertion 604 may record a subsequent a digitally signed assertion 604 transferring some or all of the value transferred in the first a digitally signed assertion 604 to a new address in the same manner. A digitally signed assertion 604 may contain textual information that is not a transfer of some item of value in addition to, or as an alternative to, such a transfer. For instance, as described in further detail below, a digitally signed assertion 604 may indicate a confidence level associated with a distributed storage node as described in further detail below.

In an embodiment, and still referring to FIG. 6 immutable sequential listing records a series of at least a posted content in a way that preserves the order in which the at least a posted content took place. Temporally sequential listing may be accessible at any of various security settings; for instance, and without limitation, temporally sequential listing may be readable and modifiable publicly, may be publicly readable but writable only by entities and/or devices having access privileges established by password protection, confidence level, or any device authentication procedure or facilities described herein, or may be readable and/or writable only by entities and/or devices having such access privileges. Access privileges may exist in more than one level, including, without limitation, a first access level or community of permitted entities and/or devices having ability to read, and a second access level or community of permitted entities and/or devices having ability to write; first and second community may be overlapping or non-overlapping. In an embodiment, posted content and/or immutable sequential listing may be stored as one or more zero knowledge sets (ZKS), Private Information Retrieval (PIR) structure, or any other structure that allows checking of membership in a set by querying with specific properties. Such database may incorporate protective measures to ensure that malicious actors may not query the database repeatedly in an effort to narrow the members of a set to reveal uniquely identifying information of a given posted content.

Still referring to FIG. 6, immutable sequential listing may preserve the order in which the at least a posted content took place by listing them in chronological order; alternatively or additionally, immutable sequential listing may organize digitally signed assertions 604 into sub-listings 608 such as "blocks" in a blockchain, which may be themselves collected in a temporally sequential order; digitally signed assertions 604 within a sub-listing 608 may or may not be temporally sequential. The ledger may preserve the order in which at least a posted content took place by listing it in sub-listings 608 and placing the sub-listings 608 in chronological order. The immutable sequential listing may be a distributed, consensus-based ledger, such as those operated according to the protocols promulgated by Ripple Labs, Inc., of San Francisco, Calif., or the Stellar Development Foundation, of San Francisco, Calif, or of Thunder Consensus. In some embodiments, the ledger is a secured ledger; in one embodiment, a secured ledger is a ledger having safeguards against alteration by unauthorized parties. The ledger may be maintained by a proprietor, such as a system administrator on a server, that controls access to the ledger; for instance, the user account controls may allow contributors to the ledger to add at least a posted content to the ledger but may not allow any users to alter at least a posted content that have been added to the ledger. In some embodiments, ledger is cryptographically secured; in one embodiment, a ledger is cryptographically secured where each link in the chain contains encrypted or hashed information that makes it practically infeasible to alter the ledger without betraying that alteration has taken place, for instance by requiring that an administrator or other party sign new additions to the chain with a digital signature. Immutable sequential listing may be incorporated in, stored in, or incorporate, any suitable data structure, including without limitation any database, datastore, file structure, distributed hash table, directed acyclic graph or the like. In some embodiments, the timestamp of an entry is cryptographically secured and validated via trusted time, either directly on the chain or indirectly by utilizing a separate chain. In one embodiment the validity of timestamp is provided using a time stamping authority as described in the RFC 3161 standard for trusted timestamps, or in the ANSI ASC x9.95 standard. In another embodiment, the trusted time ordering is provided by a group of entities collectively acting as the time stamping authority with a requirement that a threshold number of the group of authorities sign the timestamp.

In some embodiments, and with continued reference to FIG. 6, immutable sequential listing, once formed, may be inalterable by any party, no matter what access rights that party possesses. For instance, immutable sequential listing may include a hash chain, in which data is added during a successive hashing process to ensure non-repudiation. Immutable sequential listing may include a block chain. In one embodiment, a block chain is immutable sequential listing that records one or more new at least a posted content in a data item known as a sub-listing 608 or "block." An example of a block chain is the BITCOIN block chain used to record BITCOIN transactions and values. Sub-listings 608 may be created in a way that places the sub-listings 608 in chronological order and link each sub-listing 608 to a previous sub-listing 608 in the chronological order so that any computing device may traverse the sub-listings 608 in reverse chronological order to verify any at least a posted content listed in the block chain. Each new sub-listing 608 may be required to contain a cryptographic hash describing the previous sub-listing 608. In some embodiments, the block chain contains a single first sub-listing 608 sometimes known as a "genesis block."

Still referring to FIG. 6, the creation of a new sub-listing 608 may be computationally expensive; for instance, the creation of a new sub-listing 608 may be designed by a "proof of work" protocol accepted by all participants in forming the immutable sequential listing to take a powerful set of computing devices a certain period of time to produce. Where one sub-listing 608 takes less time for a given set of computing devices to produce the sub-listing 608 protocol may adjust the algorithm to produce the next sub-listing 608 so that it will require more steps; where one sub-listing 608 takes more time for a given set of computing devices to produce the sub-listing 608 protocol may adjust the algorithm to produce the next sub-listing 608 so that it will require fewer steps. As an example, protocol may require a new sub-listing 608 to contain a cryptographic hash describing its contents; the cryptographic hash may be required to satisfy a mathematical condition, achieved by having the sub-listing 608 contain a number, called a nonce, whose value is determined after the fact by the discovery of the hash that satisfies the mathematical condition. Continuing the example, the protocol may be able to adjust the mathematical condition so that the discovery of the hash describing a sub-listing 608 and satisfying the mathematical condition requires more or less steps, depending on the outcome of the previous hashing attempt. Mathematical condition, as an example, might be that the hash contains a certain number of leading zeros and a hashing algorithm that requires more steps to find a hash containing a greater number of leading zeros, and fewer steps to find a hash containing a lesser number of leading zeros. In some embodiments, production of a new sub-listing 608 according to the protocol is known as "mining." The creation of a new sub-listing 608 may be designed by a "proof of stake" protocol as will be apparent to those skilled in the art upon reviewing the entirety of this disclosure.

Continuing to refer to FIG. 6, in some embodiments, protocol also creates an incentive to mine new sub-listings 608. The incentive may be financial; for instance, successfully mining a new sub-listing 608 may result in the person or entity that mines the sub-listing 608 receiving a predetermined amount of currency. The currency may be fiat currency. Currency may be cryptocurrency as defined below. In other embodiments, incentive may be redeemed for particular products or services; the incentive may be a gift certificate with a particular business, for instance. In some embodiments, incentive is sufficiently attractive to cause participants to compete for the incentive by trying to race each other to the creation of sub-listings 608 Each sub-listing 608 created in immutable sequential listing may contain a record or at least a posted content describing one or more addresses that receive an incentive, such as virtual currency, as the result of successfully mining the sub-listing 608.

With continued reference to FIG. 6, where two entities simultaneously create new sub-listings 608, immutable sequential listing may develop a fork; protocol may determine which of the two alternate branches in the fork is the valid new portion of the immutable sequential listing by evaluating, after a certain amount of time has passed, which branch is longer. "Length" may be measured according to the number of sub-listings 608 in the branch. Length may be measured according to the total computational cost of producing the branch. Protocol may treat only at least a posted content contained the valid branch as valid at least a posted content. When a branch is found invalid according to this protocol, at least a posted content registered in that branch may be recreated in a new sub-listing 608 in the valid branch; the protocol may reject "double spending" at least a posted content that transfer the same virtual currency that another at least a posted content in the valid branch has already transferred. As a result, in some embodiments the creation of fraudulent at least a posted content requires the creation of a longer immutable sequential listing branch by the entity attempting the fraudulent at least a posted content than the branch being produced by the rest of the participants; as long as the entity creating the fraudulent at least a posted content is likely the only one with the incentive to create the branch containing the fraudulent at least a posted content, the computational cost of the creation of that branch may be practically infeasible, guaranteeing the validity of all at least a posted content in the immutable sequential listing.

Still referring to FIG. 6, additional data linked to at least a posted content may be incorporated in sub-listings 608 in the immutable sequential listing; for instance, data may be incorporated in one or more fields recognized by block chain protocols that permit a person or computer forming at least a posted content to insert additional data in the immutable sequential listing. In some embodiments, additional data is incorporated in an unspendable at least a posted content field. For instance, the data may be incorporated in an OP_RETURN within the BITCOIN block chain. In other embodiments, additional data is incorporated in one signature of a multi-signature at least a posted content. In an embodiment, a multi-signature at least a posted content is at least a posted content to two or more addresses. In some embodiments, the two or more addresses are hashed together to form a single address, which is signed in the digital signature of the at least a posted content. In other embodiments, the two or more addresses are concatenated. In some embodiments, two or more addresses may be combined by a more complicated process, such as the creation of a Merkle tree or the like. In some embodiments, one or more addresses incorporated in the multi-signature at least a posted content are typical crypto-currency addresses, such as addresses linked to public keys as described above, while one or more additional addresses in the multi-signature at least a posted content contain additional data related to the at least a posted content; for instance, the additional data may indicate the purpose of the at least a posted content, aside from an exchange of virtual currency, such as the item for which the virtual currency was exchanged. In some embodiments, additional information may include network statistics for a given node of network, such as a distributed storage node, e.g. the latencies to nearest neighbors in a network graph, the identities or identifying information of neighboring nodes in the network graph, the trust level and/or mechanisms of trust (e.g. certificates of physical encryption keys, certificates of software encryption keys, (in non-limiting example certificates of software encryption may indicate the firmware version, manufacturer, hardware version and the like), certificates from a trusted third party, certificates from a decentralized anonymous authentication procedure, and other information quantifying the trusted status of the distributed storage node) of neighboring nodes in the network graph, IP addresses, GPS coordinates, and other information informing location of the node and/or neighboring nodes, geographically and/or within the network graph. In some embodiments, additional information may include history and/or statistics of neighboring nodes with which the node has interacted. In some embodiments, this additional information may be encoded directly, via a hash, hash tree or other encoding.

With continued reference to FIG. 6, in some embodiments, virtual currency is traded as a crypto-currency. In one embodiment, a crypto-currency is a digital, currency such as Bitcoins, Peercoins, Namecoins, and Litecoins. Crypto-currency may be a clone of another crypto-currency. The crypto-currency may be an "alt-coin." Crypto-currency may be decentralized, with no particular entity controlling it; the integrity of the crypto-currency may be maintained by adherence by its participants to established protocols for exchange and for production of new currency, which may be enforced by software implementing the crypto-currency. Crypto-currency may be centralized, with its protocols enforced or hosted by a particular entity. For instance, crypto-currency may be maintained in a centralized ledger, as in the case of the XRP currency of Ripple Labs, Inc., of San Francisco, Calif. In lieu of a centrally controlling authority, such as a national bank, to manage currency values, the number of units of a particular crypto-currency may be limited; the rate at which units of crypto-currency enter the market may be managed by a mutually agreed-upon process, such as creating new units of currency when mathematical puzzles are solved, the degree of difficulty of the puzzles being adjustable to control the rate at which new units enter the market. Mathematical puzzles may be the same as the algorithms used to make productions of sub-listings 608 in a block chain computationally challenging; the incentive for producing sub-listings 608 may include the grant of new crypto-currency to the miners. Quantities of crypto-currency may be exchanged using at least a posted content as described above.

Figure 7:
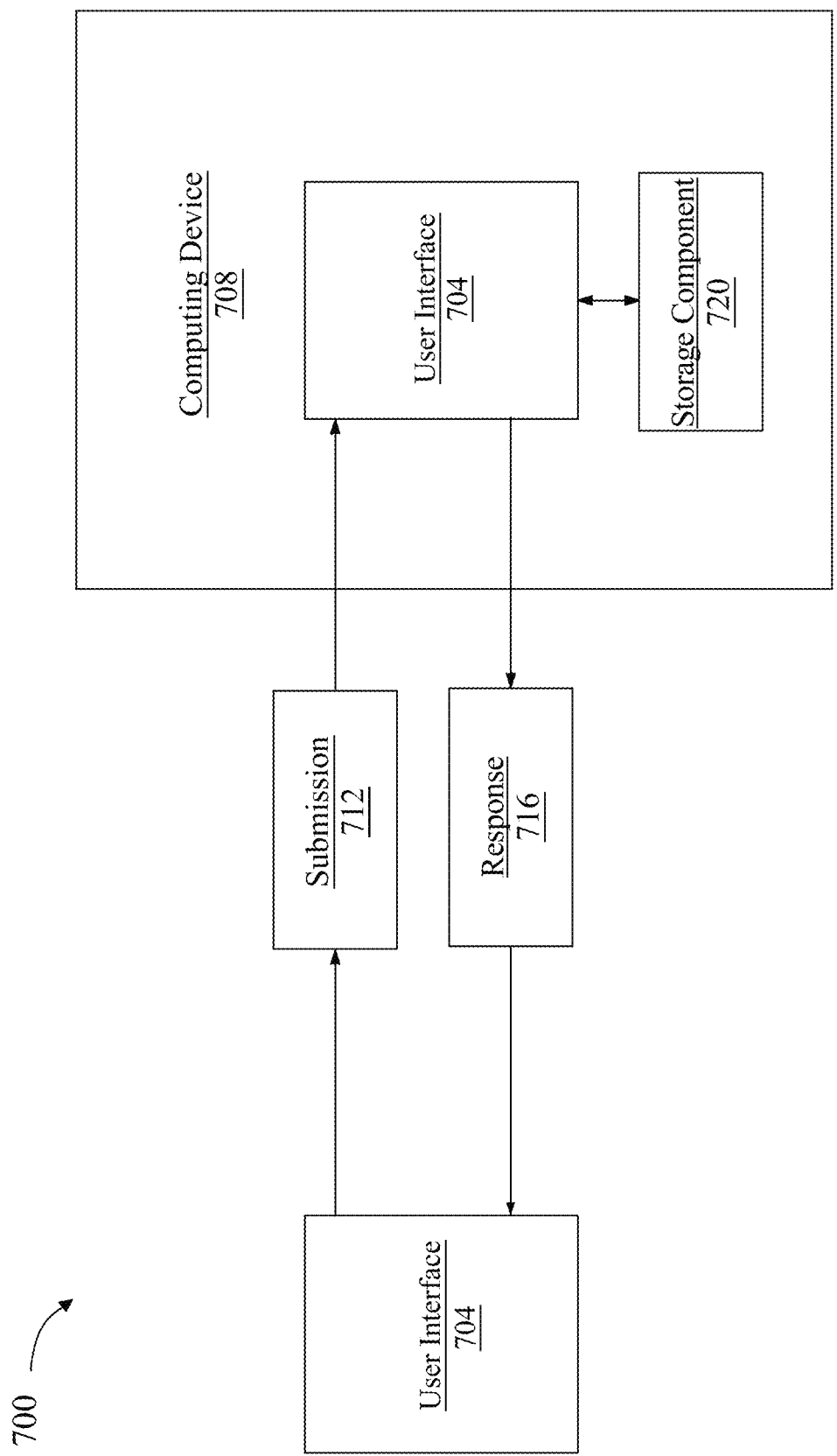
FIG. 7 is a block diagram illustrating an exemplary embodiment of a chatbot.

Referring to FIG. 7, a chatbot system 700 is schematically illustrated. According to some embodiments, a user interface 704 may be communicative with a computing device 708 that is configured to operate a chatbot. In some cases, user interface 704 may be local to computing device 708. Alternatively or additionally, in some cases, user interface 704 may remote to computing device 708 and communicative with the computing device 708, by way of one or more networks, such as without limitation the internet. Alternatively or additionally, user interface 704 may communicate with user device 708 using telephonic devices and networks, such as without limitation fax machines, short message service (SMS), or multimedia message service (MMS). Commonly, user interface 704 communicates with computing device 708 using text-based communication, for example without limitation using a character encoding protocol, such as American Standard for Information Interchange (ASCII). Typically, a user interface 704 conversationally interfaces a chatbot, by way of at least a submission 712, from the user interface 708 to the chatbot, and a response 716, from the chatbot to the user interface 704. In many cases, one or both of submission 712 and response 716 are text-based communication. Alternatively or additionally, in some cases, one or both of submission 712 and response 716 are audio-based communication.

Continuing in reference to FIG. 7, a submission 712 once received by computing device 708 operating a chatbot, may be processed by a processor. In some embodiments, processor processes a submission 712 using one or more of keyword recognition, pattern matching, and natural language processing. In some embodiments, processor employs real-time learning with evolutionary algorithms. In some cases, processor may retrieve a pre-prepared response from at least a storage component 720, based upon submission 712. Alternatively or additionally, in some embodiments, processor communicates a response 716 without first receiving a submission 712, thereby initiating conversation. In some cases, processor communicates an inquiry to user interface 704; and the processor is configured to process an answer to the inquiry in a following submission 712 from the user interface 704. In some cases, an answer to an inquiry present within a submission 712 from a user device 704 may be used by computing device 708 as an input to another function.

With continued reference to FIG. 7, A chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "Chatbot input" is any response that a candidate or employer inputs in to a chatbot as a response to a prompt or question.

With continuing reference to FIG. 7, computing device 708 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 708 may generate two or more decision trees, which may overlap; for instance, a root node of one tree may connect to and/or receive output from one or more terminal nodes of another tree, intermediate nodes of one tree may be shared with another tree, or the like.

Still referring to FIG. 7, computing device 708 may build decision tree by following relational identification; for example, relational indication may specify that a first rule module receives an input from at least a second rule module and generates an output to at least a third rule module, and so forth, which may indicate to computing device 708 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 708 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 7, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 8:
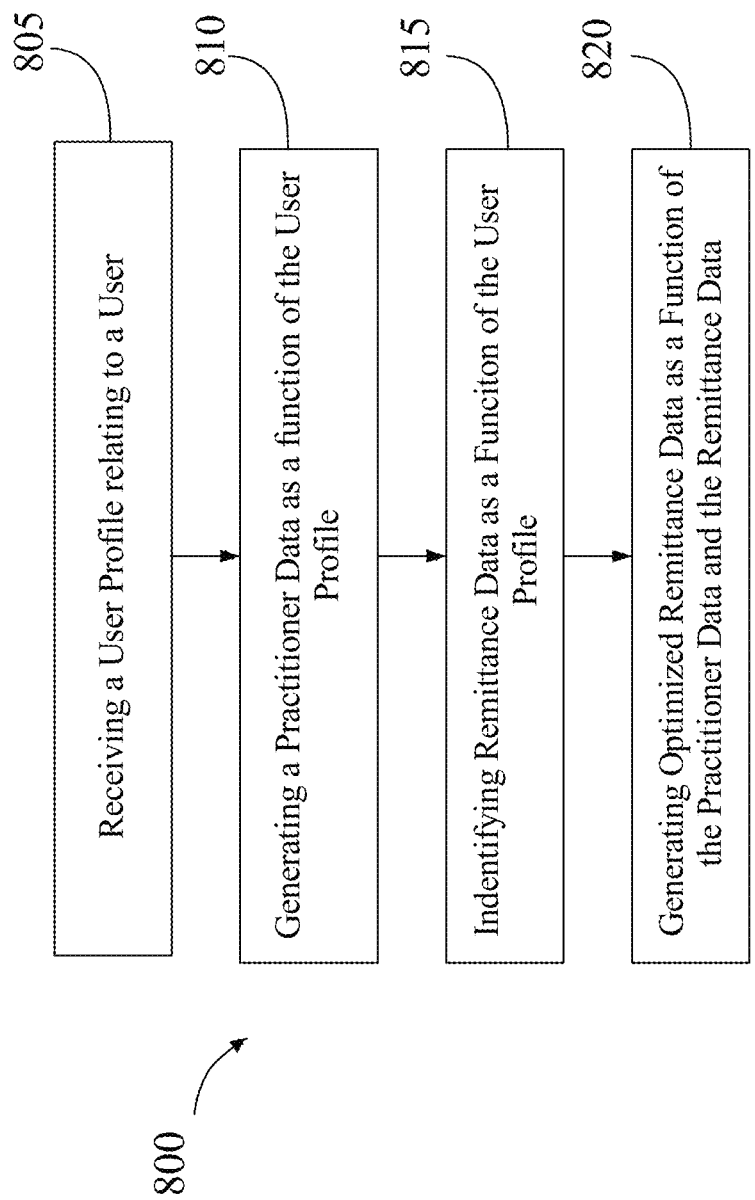
FIG. 8 is a flow diagram of an exemplary method for data fault detection and repair.

Referring now to FIG. 8, a flow diagram of an exemplary method 800 for data fault detection and repair is illustrated. At step 805, method 800 includes receiving, using at least a processor, a user profile relating to a user, wherein the user profile comprises at least provider data of a user. This may be implemented as described and with reference to FIGS. 1-7. In some embodiments, the user profile maybe received from an application programming interface and/or a web crawler.

Still referring to FIG. 8, at step 810, method 800 includes generating, using the at least a processor, practitioner data as a function of the user profile. This may be implemented as described and with reference to FIGS. 1-7. In some embodiments, practitioner data may comprise at least a procedure data and/or a medical transport data.

Still referring to FIG. 8, at step 815, method 800 includes identifying, using the at least a processor, remittance data as a function of the practitioner data. This may be implemented as described and with reference to FIGS. 1-7. In some embodiments, the remittance data may comprise a data category code. Generating the data fault may further comprise classifying a data category code to the provider data.

Still referring to FIG. 8, at step 820, method 800 includes generating, using the at least a processor, data fault as a function of the practitioner data and the remittance data. This may be implemented as described and with reference to FIGS. 1-7. In some embodiments, the data fault is generated using a fault classifier. In other embodiments, the data fault comprise a remittance score.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
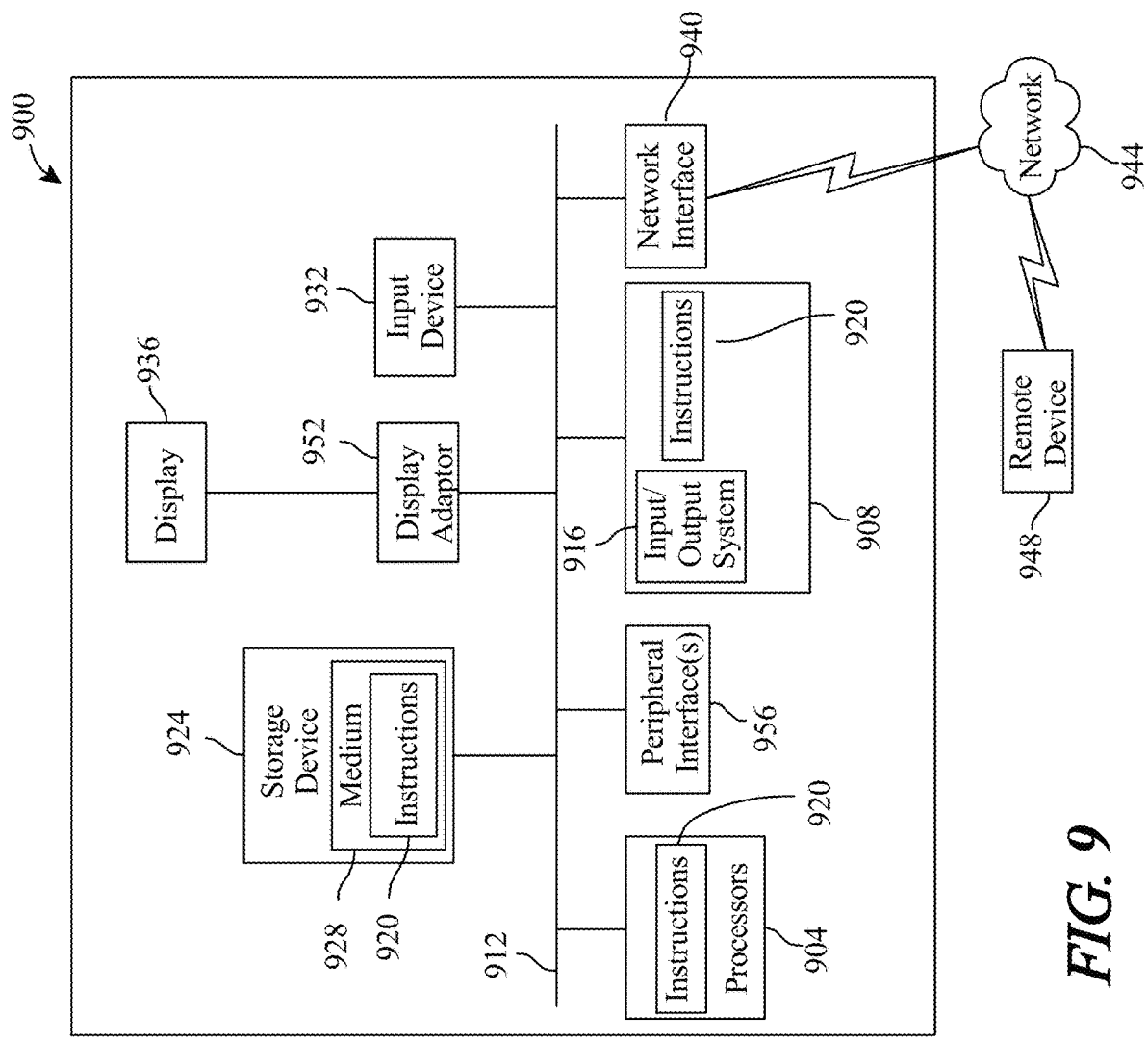
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for data fault detection and repair, wherein the apparatus comprises:
   at least a processor; and a memory communicatively connected to the at least a processor, the memory containing instructions configuring the at least a processor to:
  receive a user profile relating to a user, wherein the user profile comprises provider data of the user;
  generate practitioner data as a function of the user profile, wherein the practitioner data comprises procedure data and a cost of medical transportation;
  identify remittance data as a function of the practitioner data, wherein identifying the remittance data comprises:
    generating a financial responsibility identification, wherein generating the financial responsibility identification includes comparing the provider data of the user to the practitioner data; and
    identifying at least a data category code assigned to the user;
  identify at least one data fault in the remittance data, wherein identifying the data fault comprises comparing the procedure data to the at least a data category code;
  generate a data fault rank for the at least one data fault as a function of the cost of medical transportation, wherein generating the data fault rank further comprises:
    iteratively training a machine learning model wherein the machine learning model is trained using rank training data wherein the rank training data comprises at least one data fault input and at least a data fault rank output;
    updating the rank training data as a function of a correlation between the at least one data fault input and the at least a data fault rank output; and
    retraining the machine learning model as a function of an updated rank training data; and
  initiate a data correction action comprising automatically disputing wrongful charges to the user based on the identified data fault and the data fault rank; and
  display the data fault and the data correction action to the user using a graphical user interface.

2. The apparatus of claim 1, wherein receiving the user profile comprises receiving the user profile using an application programming interface (API).

3. The apparatus of claim 1, wherein receiving the user profile comprises receiving the user profile using a web crawler.

4. The apparatus of claim 1, wherein receiving the user profile comprises receiving the user profile using a chatbot.

5. The apparatus of claim 1, wherein the remittance data comprises at least one data category code.

6. The apparatus of claim 5, wherein identifying the data fault further comprises:
  classifying the at least one data category code to the provider data; and
  identifying the data fault as a function of the classification.

7. The apparatus of claim 1, wherein identifying the data fault comprises identifying the data fault using a fault classifier.

8. The apparatus of claim 1, wherein the data correction action comprises providing a notification to a provider of a procedure as a function of the practitioner data.

9. The apparatus of claim 1, wherein the procedure data comprises at least an itemized medical bill.

10. A method for data fault detection and repair, wherein the method comprises:
  receiving, by at least a processor, a user profile relating to a user, wherein the user profile comprises provider data of the user;
  generating, by the at least a processor, practitioner data as a function of the user profile, wherein the practitioner data comprises procedure data and a cost of medical transportation;
  identifying, by the at least a processor, remittance data as a function of the practitioner data, wherein identifying the remittance data comprises:
    generating a financial responsibility identification, wherein generating the financial responsibility identification includes comparing the provider data of the user to the practitioner data; and
    identifying at least a data category code assigned to the user;
  identifying, by the at least a processor, at least one data fault in the remittance data, wherein identifying the data fault comprises comparing the procedure data to the at least a data category code;
  generating, by the at least a processor, a data fault rank for the at least one data fault as a function of the cost of medical transportation, wherein generating the data fault rank further comprises:
    iteratively training a machine learning model wherein the machine learning model is trained using rank training data wherein the rank training data comprises at least one data fault input and at least a data fault rank output;
    updating the rank training data as a function of a correlation between the at least one data fault input and the at least a data fault rank output; and
    retraining the machine learning model as a function of an updated rank training data; and
  initiating, by the at least a processor, a data correction action comprising automatically disputing wrongful charges to the user based on the identified data fault and data fault rank; and
  displaying, by the at least a processor, the data fault and the data correction action to the user using a graphical user interface.

11. The method of claim 10, wherein receiving the user profile comprises receiving the user profile using an application programming interface (API).

12. The method of claim 10, wherein receiving the user profile comprises receiving the user profile using a web crawler.

13. The method of claim 10, wherein receiving the user profile comprises receiving the user profile using a chatbot.

14. The method of claim 10, wherein the remittance data comprises at least one data category code.

15. The method of claim 14, wherein identifying the data fault further comprises:
  classifying the data category code to the provider data; and
  identifying the data fault as a function of the classification.

16. The method of claim 10, wherein identifying the data fault comprises identifying the data fault using a fault classifier.

17. The method of claim 10, wherein the data fault comprises providing a notification to a provider of a procedure as a function of the practitioner data.

18. The method of claim 10, wherein the procedure data comprises at least an itemized medical bill.

* * * * *